(12) United States Patent
Kamiya

(10) Patent No.: US 9,459,197 B2
(45) Date of Patent: Oct. 4, 2016

(54) METHOD FOR MEASURING DYNAMIC VISCOELASTICITY OF PARTICULATE MATERIAL

(75) Inventor: Kazunobu Kamiya, Tochigi (JP)

(73) Assignee: DEXERIALS CORPORATION, Tokyo (JP)

(*) Notice: Subject to any disclaimer, the term of this patent is extended or adjusted under 35 U.S.C. 154(b) by 241 days.

(21) Appl. No.: 14/124,492

(22) PCT Filed: Jul. 18, 2012

(86) PCT No.: PCT/JP2012/068146
§ 371 (c)(1),
(2), (4) Date: Dec. 6, 2013

(87) PCT Pub. No.: WO2013/015160
PCT Pub. Date: Jan. 31, 2013

(65) Prior Publication Data
US 2014/0102223 A1 Apr. 17, 2014

(30) Foreign Application Priority Data
Jul. 25, 2011 (JP) .................................. 2011-162016

(51) Int. Cl.
*G01N 19/00* (2006.01)
*G01N 19/04* (2006.01)
(Continued)

(52) U.S. Cl.
CPC ............... *G01N 19/00* (2013.01); *G01N 3/32* (2013.01); *G01N 19/04* (2013.01);
(Continued)

(58) Field of Classification Search
CPC . G01N 3/32; G01N 19/04; G01N 2001/2833
See application file for complete search history.

(56) References Cited

U.S. PATENT DOCUMENTS

| 5,452,614 A | 9/1995 | Kato et al. |
| 2002/0031645 A1* | 3/2002 | Sano ................... B05D 1/00 428/143 |

(Continued)

FOREIGN PATENT DOCUMENTS

| JP | A-6-123696 | 5/1994 |
| JP | A-8-221741 | 8/1996 |

(Continued)

OTHER PUBLICATIONS

Apr. 10, 2015 Office Action issued in Chinese Application No. 201280036784.2.
(Continued)

*Primary Examiner* — Paul West
(74) *Attorney, Agent, or Firm* — Oliff PLC

(57) ABSTRACT

A method for measuring a dynamic viscoelasticity of a particulate material uses, as a sample to be subjected to the dynamic viscoelasticity measurement, a sheet-shaped test piece in which the particulate material to be measured is attached to an adhesion layer formed on a heat-resistant sheet base material. With regard to the measurement conditions of the dynamic viscoelasticity measurement, the measurement temperature is within a predetermined temperature range of from −150 to 300° C., the heating rate is a constant rate ranging from 0.01 to 100° C./minute, the measurement frequency is a constant frequency ranging from 0.01 to 100 Hz, and a sine wave control tensile mode is employed. When the particulate material is attached to the adhesion layer, the particulate material crushed in advance is sprinkled on one side of the adhesion layer and then the particulate material-sprinkled surface is squeegeed and/or air-blown.

8 Claims, 20 Drawing Sheets

(51) Int. Cl.
*G01N 3/32* (2006.01)
*G01N 1/28* (2006.01)

(52) U.S. Cl.
CPC ............... *G01N 2001/2833* (2013.01); *G01N 2203/0005* (2013.01); *G01N 2203/0094* (2013.01); *G01N 2203/0224* (2013.01); *G01N 2203/0298* (2013.01)

(56) References Cited

U.S. PATENT DOCUMENTS

| | | | | |
|---|---|---|---|---|
| 2007/0178408 | A1* | 8/2007 | Yamada | G03F 7/18 430/300 |
| 2008/0083909 | A1 | 4/2008 | Sato et al. | |
| 2011/0111173 | A1* | 5/2011 | Ogawa | C23C 24/08 428/141 |

FOREIGN PATENT DOCUMENTS

| | | |
|---|---|---|
| JP | A-8-231731 | 9/1996 |
| JP | A-2005-232297 | 9/2005 |
| JP | A-2007-86062 | 4/2007 |
| JP | A-2008-186761 | 8/2008 |
| JP | A-2009-64043 | 3/2009 |
| JP | A-2009-221465 | 10/2009 |
| JP | B2-4381255 | 12/2009 |
| JP | A-2010-74006 | 4/2010 |

OTHER PUBLICATIONS

Nov. 4, 2014 Office Action issued in Chinese Patent Application No. 201280036784.2.
International Search Report issued in International Patent Application No. PCT/JP2012/068146 dated Oct. 16, 2012.
Feb. 18, 2015 Extended Search Report issued in European Application No. 12817168.3.

* cited by examiner

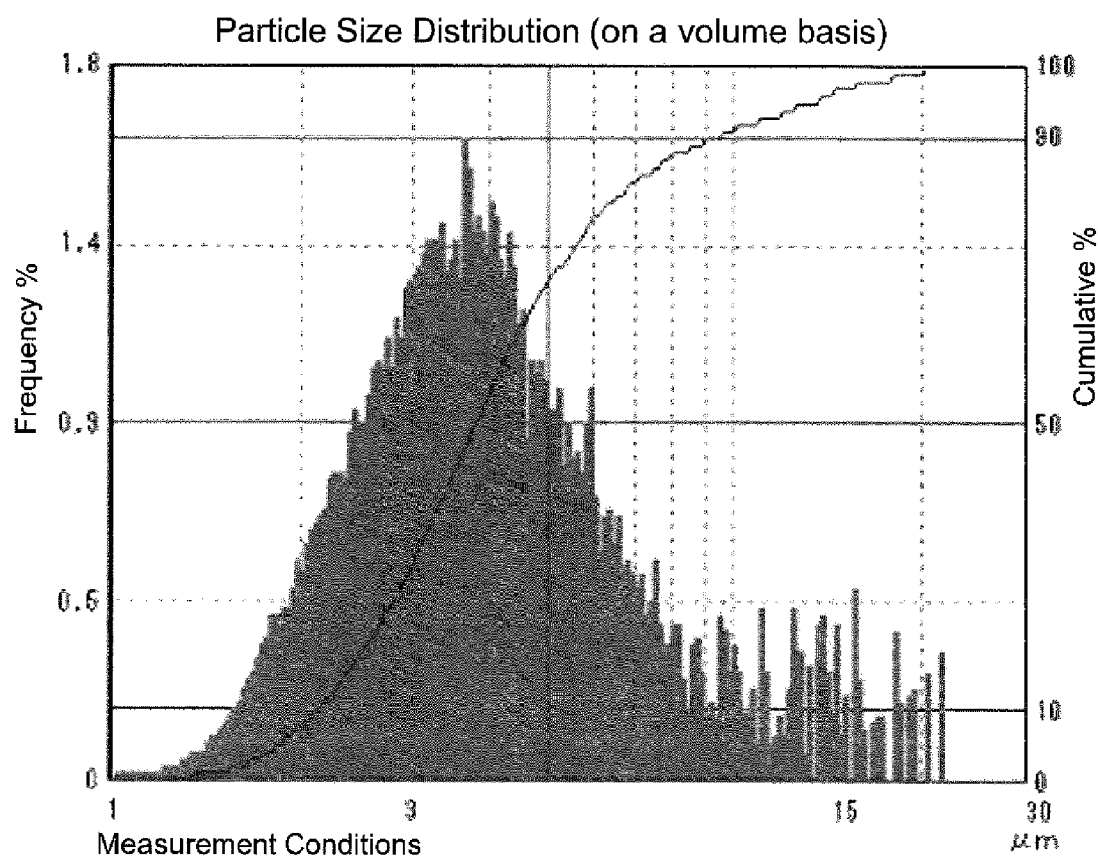

METHOD FOR MEASURING DYNAMIC VISCOELASTICITY OF PARTICULATE MATERIAL

TECHNICAL FIELD

The present invention relates to a method for measuring a dynamic viscoelasticity of a particulate material.

BACKGROUND ART

Differential scanning calorimetry (DSC) has been often used for determining the glass transition temperature of resin materials, but may fail to detect a signal originated from glass transition depending on the types of materials in some cases. Although, such cases have a drawback in that a relatively large amount of a material to be measured had to be prepared and formed into a sheet-shaped test piece or a fiber-shaped test piece, the loss tangent tan δ of those test pieces has been determined by dynamic viscoelasticity measurement in a tensile mode and the temperature at the maximum peak has been taken as the glass transition temperature of the measured resin material.

For a fine resin particulate material as used as a filler, by the way, the dynamic viscoelasticity measurement had to be performed inevitably because the aggregation of powders had a low thermal conductivity and thus the DSC failed to detect a signal originated from glass transition. However, being in the form of the fine particulate material has caused a problem with the dynamic viscoelasticity measurement either in a tensile mode or in a shear mode or in a three-point bending mode.

Accordingly, the dynamic viscoelasticity measurement of such fine resin particulate materials has required production of a sample having a shape capable of undergoing the dynamic viscoelasticity measurement. For example, it has been proposed that a composition in which 50 to 150 parts by mass of polymer resin particles are blended with 100 parts by mass of thermosetting epoxy resin is poured into a strip-shaped mold and cured to produce a strip-shaped test piece (Patent Literature 1). Furthermore, it has been proposed that a dispersion obtained by dispersing 100 parts by mass of acrylic polymer particles in 100 parts by mass of diisononyl phthalate was casted and heated to produce a sheet-shaped test piece (Patent Literature 2).

CITATION LIST

Patent Literature

Patent Literature 1: Japanese Patent Application Laid-Open No. Hei. 8-231731
Patent Literature 2: Japanese Patent Application Laid-Open No. 2005-232297

SUMMARY OF INVENTION

Technical Problem

The techniques in Patent Literatures 1 and 2, however, have required not only a relatively large amount of a resin particulate material but also complicated processes such as steps of preparing, casting, forming, and heating the dispersion containing the particulate material, when producing the sheet-shaped test piece for the dynamic viscoelasticity measurement of the particulate material. Accordingly, there have been such problems that the time for the dynamic viscoelasticity measurement including the production time of the sheet-shaped test piece increased and the cost for the measurement also increased.

The present invention addresses the above-mentioned problems of the conventional techniques. It is an object of the present invention to shorten the time for the dynamic viscoelasticity measurement including the production time of the sheet-shaped test piece and also reduce the cost for the measurement by simply producing a test piece capable of undergoing the dynamic viscoelasticity measurement in a short time with low cost when the particulate material is subjected to the dynamic viscoelasticity measurement.

Solution to Problem

The present inventors have found that the dynamic viscoelasticity measurement of a sheet piece obtained by attaching a particulate material to be measured to an adhesion layer of a heat-resistant sheet base material having the adhesion layer formed thereon allows observation of the maximum peak other than the maximum peaks of loss tangent tan δ originated from the heat-resistant sheet base material and the adhesion layer (i.e., the maximum peak of loss tangent tan δ originated from the particulate material). This finding has led to complete the present invention.

Specifically, the present invention provides a method for measuring a dynamic viscoelasticity of a particulate material, wherein the method uses a sheet-shaped test piece as a sample to be subjected to dynamic viscoelasticity measurement, the sheet-shaped test piece comprising a heat-resistant sheet base material, an adhesion layer, and a particulate material to be measured, the adhesion layer being formed on the heat-resistant sheet base material, and the particulate material being attached to the adhesion layer.

Advantageous Effects of Invention

In the method for measuring a dynamic viscoelasticity of a particulate material of the present invention, as a sample to be subjected to the dynamic viscoelasticity measurement, used is the sheet-shaped test piece in which the particulate material to be measured is attached to the adhesion layer formed on the heat-resistant sheet base material. This sheet-shaped test piece can be simply produced by a procedure such as sprinkling using a very small amount of the particulate material in a short time with low cost, and further a cheap, commercially available masking tape can be used as a sheet material in which an adhesion layer is formed on a heat-resistant sheet base material. Accordingly, it is possible to shorten the time for the dynamic viscoelasticity measurement including the production time of the sheet-shaped test piece and also reduce the cost for the measurement.

BRIEF DESCRIPTION OF DRAWINGS

FIG. 9A is a particle size distribution chart on a volume basis of a particulate material C used in Example 3.

DESCRIPTION OF EMBODIMENTS

The method for measuring a dynamic viscoelasticity of a particulate material of the present invention is characterized by using a sheet-shaped test piece in which a particulate material to be measured is attached to an adhesion layer of a heat-resistant sheet base material having the adhesion layer formed thereon as a sample to be subjected to the dynamic viscoelasticity measurement.

Figure 1:
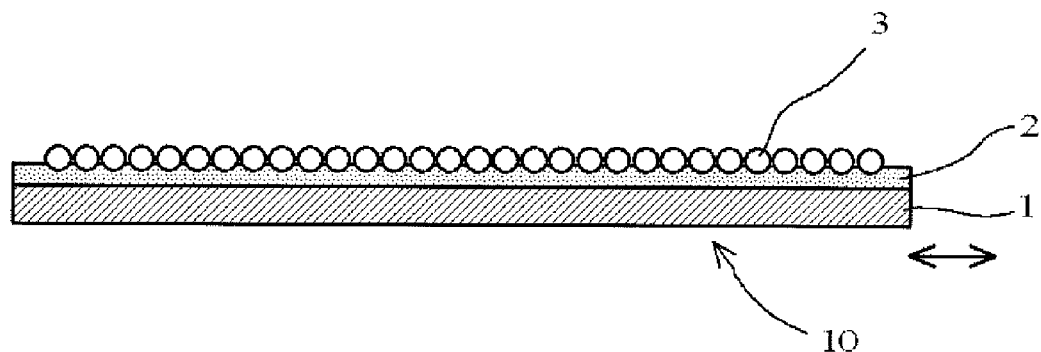
FIG. 1 is a cross-sectional view of a sheet-shaped test piece.
Figure 2:
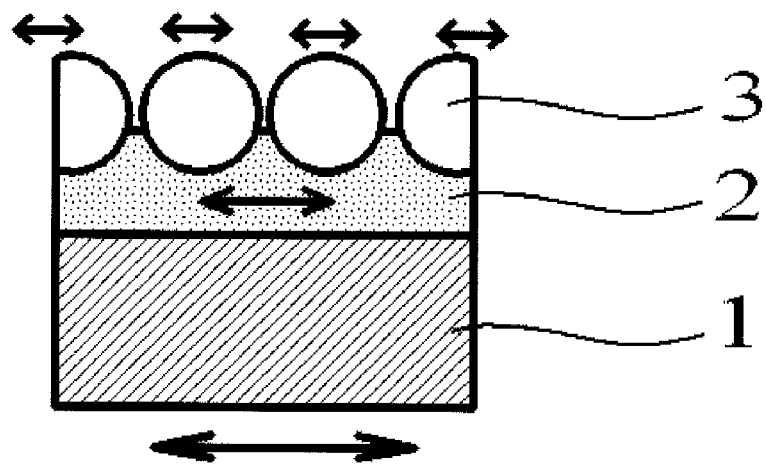
FIG. 2 is a partially enlarged view of the sheet-shaped test piece of FIG. 1.

The reason why the dynamic viscoelasticity of the particulate material can be measured by the method for measuring the dynamic viscoelasticity of the present invention is supposed as follows. Specifically, when a sheet-shaped test piece 10 in which a particulate material 3 is attached to one side of an adhesion layer 2 of a heat-resistant sheet base material 1, as shown in FIG. 1, is subjected to, for example, sinusoidal tensile deformation (arrows in the figure), the adhesion layer 2 also deforms with deformation of the heat-resistant sheet base material 1 as shown in FIG. 2. Since the particulate material 3 is held by the adhesion of the deforming adhesion layer 2, each particulate material 3 deforms with deformation of the adhesion layer 2. Therefore, the sinusoidal tensile deformation of the sheet-shaped test piece 10 causes sinusoidal tensile deformation of each particulate material 3. This is considered to enable the dynamic viscoelasticity measurement of the particulate material.

Accordingly, the amount of the particulate material 3 to be attached to the adhesion layer 2 may not be necessarily attached to the entire surface of the adhesion layer 2 as long as it is sufficient to detect dynamic viscoelasticity characteristics for the deformation. In order to achieve easy detection of the dynamic viscoelasticity characteristics, the particulate material 3 is preferably attached so as to cover the entire surface of the adhesion layer 2. Regarding a particulate material agglomerate which is not directly deformed by the adhesion layer 2, it is concerned that collapse of the agglomerate due to the deformation of the adhesion layer 2 may affect the dynamic viscoelasticity characteristics of the particulate material 3. Therefore, the particulate material 3 is preferably attached to the adhesion layer 2 in a single layer.

A well-known procedure for the dynamic viscoelasticity measurement (see JIS K7244) can be appropriately employed as the procedure for the dynamic viscoelasticity measurement used in the present invention, and a commercially available dynamic viscoelasticity measuring device can also be used as the measuring device (for example, DMS 6100, Seiko Instruments Inc.). Examples of sine wave or associated wave control deformation modes for the measurement, which can be applied to the method for measuring the dynamic viscoelasticity of the present invention, may include a tensile mode, a shear mode, a torsional shear mode, a film shear mode, and a three-point bending mode. Among them, the sine wave control tensile mode is preferred in terms of accuracy of the measurement of the sheet-shaped test piece.

Variations of the dynamic viscoelasticity measurement may include frequency dependence measurement, linear viscoelastic region measurement, temperature dependence measurement, and time dependence measurement. Herein, the frequency dependence measurement measures the dynamic viscoelasticity characteristics under a constant stress (or constant strain) while increasing the frequency, and evaluates the aggregability, entanglement, and leveling properties of the material. The linear viscoelastic region measurement measures the dynamic viscoelasticity characteristics under a constant frequency while increasing the strain (or stress), and evaluates the yield behavior of the material. The temperature dependence measurement measures the dynamic viscoelasticity characteristics under a constant strain (or constant stress) and constant frequency while continuously changing the temperature, and evaluates curing, gelation, melting, solidification, and the like of the material. The time dependence measurement measures the dynamic viscoelasticity changed with time under a constant strain (or constant stress), and quantitatively evaluates a change in curing behavior of the material due to curing conditions such as a curing wavelength and intensity.

Examples of measurement items for the dynamic viscoelasticity measurement of the present invention may include storage modulus $E'$, loss modulus $E''$, loss tangent $\tan \delta$ ($=[E''/E']$), and loss rigidity $G''$ depending on the deformation mode for the measurement and the like. The temperature exhibiting the maximum peak of loss tangent $\tan \delta$ here corresponds to the glass transition temperature of the particulate material to be measured.

Preferred measurement modes for the dynamic viscoelasticity measurement of the particulate material of the present invention may include the temperature dependence measurement in which the dynamic viscoelasticity is measured under the following measurement conditions.

The measurement temperature is within a predetermined temperature range (for example, 40 to 220° C.) of from −150 to 300° C., the heating rate is a constant rate (for example, 5° C./minute) ranging from 0.01 to 100° C./minute, the measurement frequency is a constant frequency (for example, 10 Hz) ranging from 0.01 to 100 Hz, and the sine wave control tensile mode is employed.

As a preferred example of a series of procedures of attaching the particulate material to the adhesion layer on the heat-resistant sheet base material, the particulate material is sprinkled on one side of the adhesion layer and then the particulate material-sprinkled surface is squeegeed and/or air-blown when the particulate material is attached to the adhesion layer. This example will be described below with reference to the drawings.

Figure 3A:
FIG. 3A is a cross-sectional view of an adhesive sheet used for producing the sheet-shaped test piece.

First, an adhesive sheet in which an adhesion layer 2 is formed on a heat-resistant sheet base material 1 is prepared as shown in FIG. 3A. The heat-resistant sheet base material 1 and the adhesion layer 2 each are preferably formed from a material whose maximum peak top of loss tangent tan δ does not overlap with the maximum peak top of loss tangent tan δ of the particulate material to be measured in the measurement temperature range of the dynamic viscoelasticity measurement. Furthermore, they each are more preferably formed from a material whose maximum peak of loss tangent tan δ does not appear in the measurement temperature range of the dynamic viscoelasticity measurement. This makes it easier to specify the loss tangent tan δ of the particulate material to be measured.

As specific examples of the adhesion layer 2 and the heat-resistant sheet base material 1, the adhesion layer 2 to be used can be formed from a silicone adhesive using peroxide as a curing agent and the heat-resistant sheet base material 1 to be used can be formed from a polyimide resin, when the measurement temperature range of the dynamic viscoelasticity measurement is from −50° C. to 250° C.

Figure 4A:
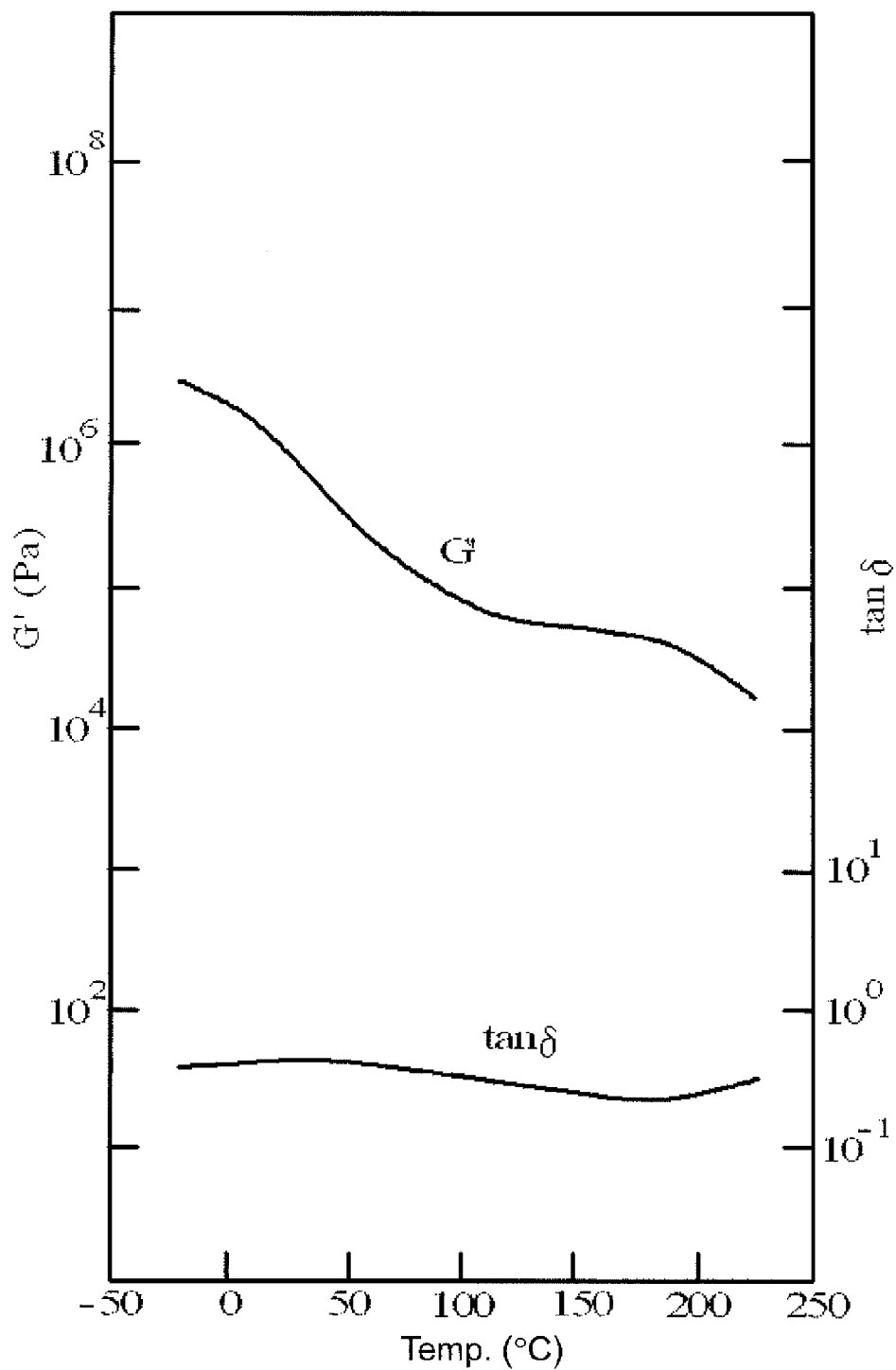
FIG. 4A is a dynamic viscoelasticity chart of a peroxide-curable type silicone adhesive.
Figure 4B:
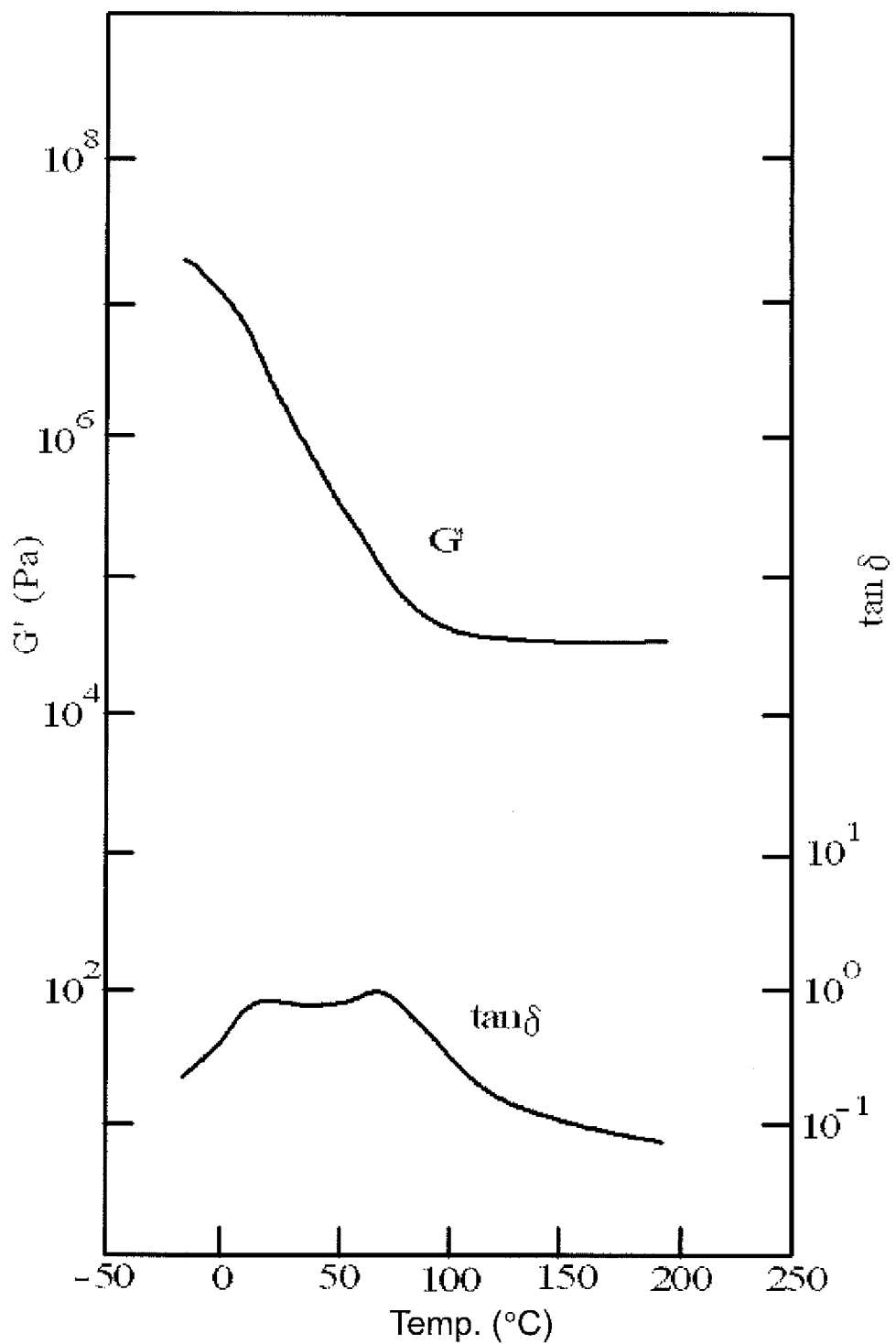
FIG. 4B is a dynamic viscoelasticity chart of an addition-curable type silicone adhesive.
Figure 4C:
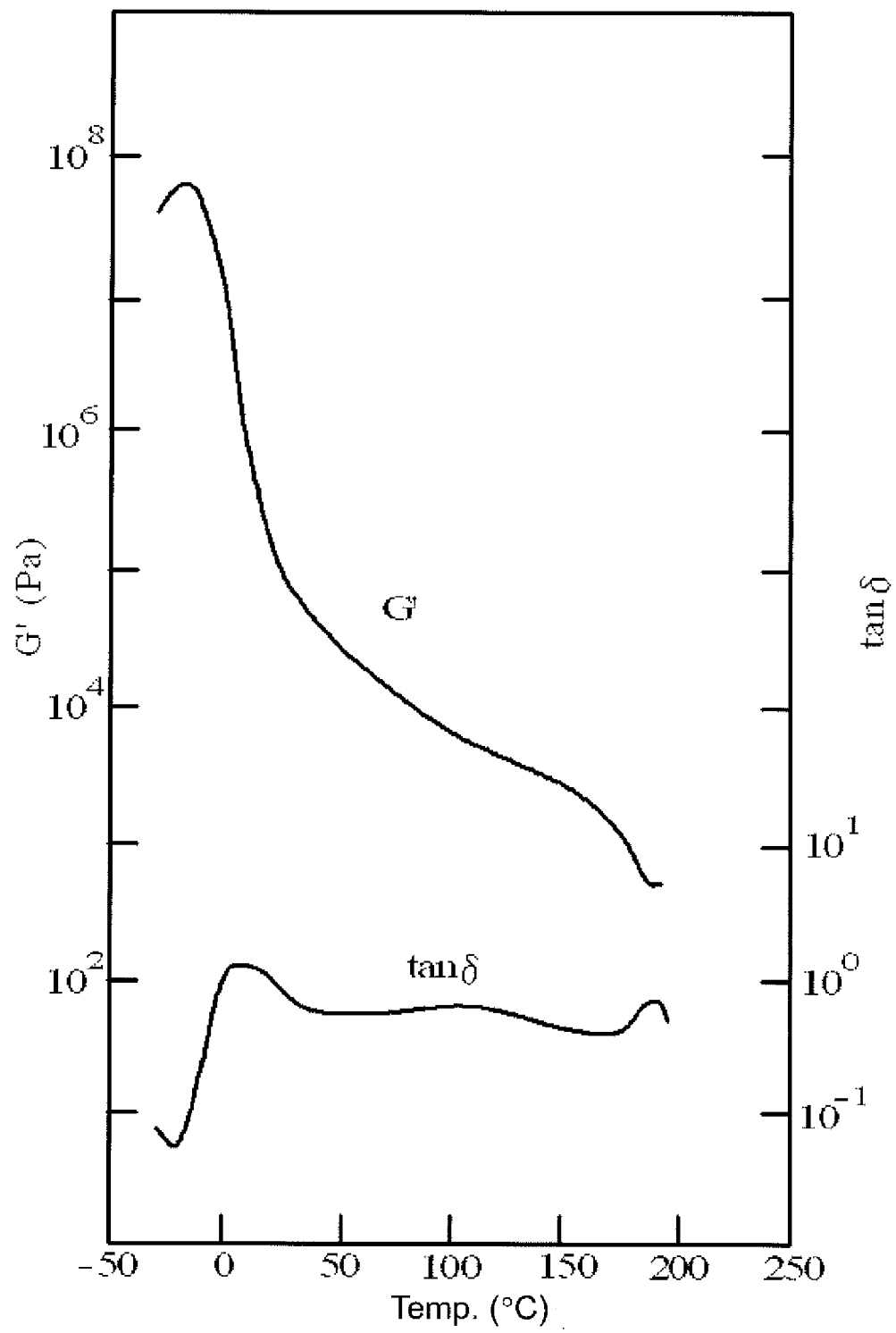
FIG. 4C is a dynamic viscoelasticity chart of a two-component type acrylic adhesive.

Accordingly, it is preferable to obtain a loss tangent tan δ chart of the target adhesive when selecting the adhesive for forming the adhesion layer 2. FIG. 4A, FIG. 4B, and FIG. 4C illustrate the loss tangent tan δ charts of the adhesives. FIG. 4A relates to a peroxide-curable type silicone adhesive, FIG. 4B relates to an addition-curable type silicone adhesive, and FIG. 4C relates to a two-component type acrylic adhesive. These figures show that the peroxide-curable type silicone adhesive in FIG. 4A has no maximum peak in the measurement temperature range in the loss tangent tan δ chart and thus can be preferably used in the method for measuring a dynamic viscoelasticity of a particulate material of the present invention. On the other hand, for the adhesives in FIG. 4B and FIG. 4C, their maximum peaks of loss tangent tan δ may overlap with the maximum peak of loss tangent tan δ of the particulate material in the measurement temperature range of the dynamic viscoelasticity measurement. Thus, when they are used in the method for measuring a dynamic viscoelasticity of a particulate material of the present invention, the range of the measurable particulate material may be significantly narrowed.

The thickness of the heat-resistant sheet base material 1 depends on the deformation mode of the dynamic viscoelasticity measurement, the physical properties of the material, and the like, and it is usually 5 μm to 1 mm and preferably 10 μm to 0.1 mm.

The thickness of the adhesion layer 2 also depends on the deformation mode of the dynamic viscoelasticity measurement, the physical properties of the material, the size of the particulate material to be measured, and the like, and it is usually 1 μm to 1 mm and preferably 1 μm to 0.1 mm.

Figure 3B:
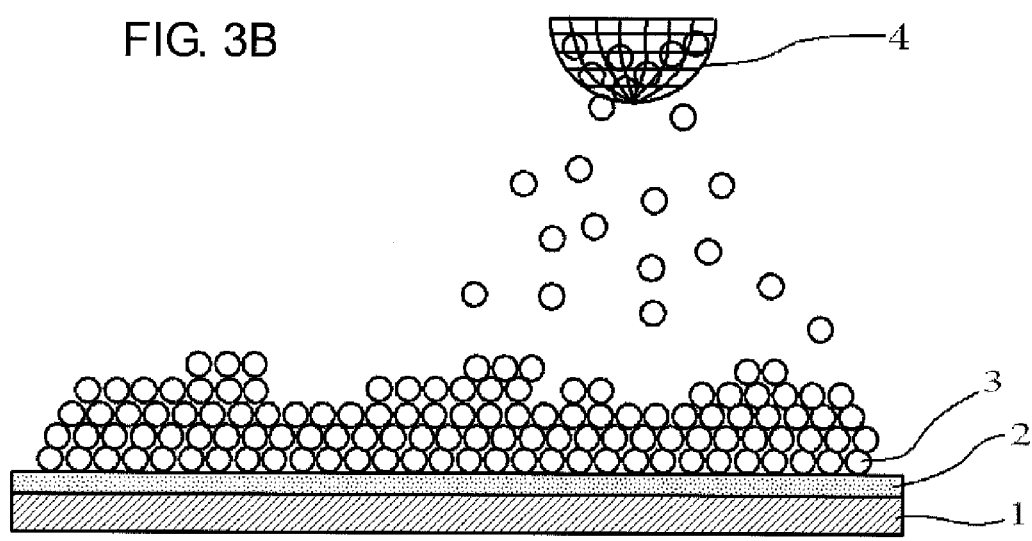
FIG. 3B is an illustrative drawing of sprinkling of the particulate material during the production of the sheet-shaped test piece.

Next, the particulate material 3 is sprinkled from above the adhesion layer 2 as shown in FIG. 3B. In this case, a sieve 4 is preferably used. The particulate material 3 is also preferably crushed in advance by a well-known procedure (for example, jet mill treatment).

Figure 3C:
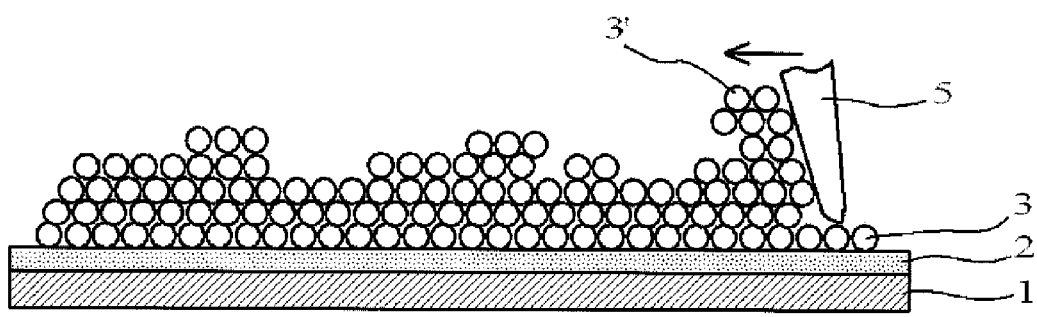
FIG. 3C is an illustrative drawing of squeegeeing during the production of the sheet-shaped test piece.
Figure 3D:
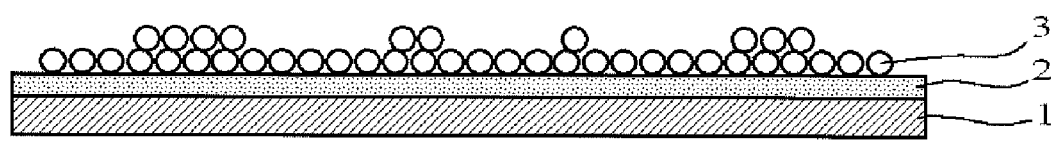
FIG. 3D is an illustrative drawing of the status of the particulate material after the squeegeeing during the production of the sheet-shaped test piece.
Figure 3E:
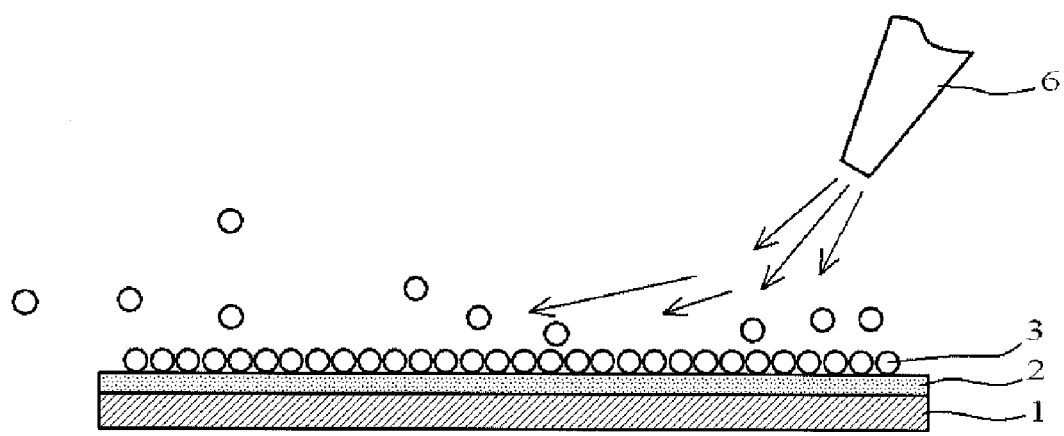
FIG. 3E is an illustrative drawing of air blow during the production of the sheet-shaped test piece.

Next, as shown in FIG. 3C, the particulate material 3 is squeegeed with a well-known squeegee 5 for printing to remove a particulate material 3' that is not directly held on the adhesion layer 2 and to cause the particulate material 3 to be held on the adhesion layer 2 so as to be pushed thereinto closely and deeply. This allows the particulate material 3 to be in the state as shown in FIG. 3D. As the squeegee 5, a rubber spatula, a metal blade, a waste rag, and the like can also be used. Next, an unnecessary particulate material is blown off by air blow from an air nozzle 6 onto a squeegeed surface as shown in FIG. 3E to provide the sheet-shaped test piece 10 suitable for the dynamic viscoelasticity measurement of the particulate material, in which the particulate material 3 is attached to the adhesion layer 2 in a single layer, as shown in FIG. 1. Regarding the squeegee and the air blow, either of them may be performed or the squeegee may be performed after the air blow, but it is preferable that the air blow be performed after the squeegee as shown in FIGS. 3A to 3E.

As the particulate material used in the method for measuring a dynamic viscoelasticity of the present invention, particles composed of various materials can be used as long as they follow deformation of the adhesion layer. For example, thermoplastic resin particles, thermosetting resin particles, cured resin particles, polysaccharide particles, protein particles, metal or ceramic coated resin particles, or the like can be used.

In addition, these particulate materials preferably have a substantially spherical shape since it is desirable that the entire particulate material 3 attached to the adhesion layer 2 be deformed in the same manner.

Regarding the size of the particulate material, a too small particulate material tends to aggregate easily and too large particulate material hardly follows deformation of the adhesion layer. The average particle size is thus preferably 0.5 to 100 μm and more preferably 1 to 30 μm.

Furthermore, for the particulate material, the coefficient of variance (CV value) of particle size distribution thereof is preferably 5 to 70% and more preferably 10 to 50%. This is because the coefficient of variance out of this range results in a broad curve of loss tangent tan δ of the particulate material, making it difficult to distinguish a definite glass transition temperature. This is considered to be because a too small or too large CV value results in a lower occupancy area ratio of the particulate material 3 on the adhesion layer 2.

Examples of such particulate materials include a particulate material in which the aluminum chelating agent is carried by porous resin particles obtained by interfacially polymerizing a polyfunctional isocyanate (Example 1 in Japanese Patent Application Laid-Open No. 2009-221465).

EXAMPLES

The present invention will be specifically described below.

Reference Example 1

Figure 5:
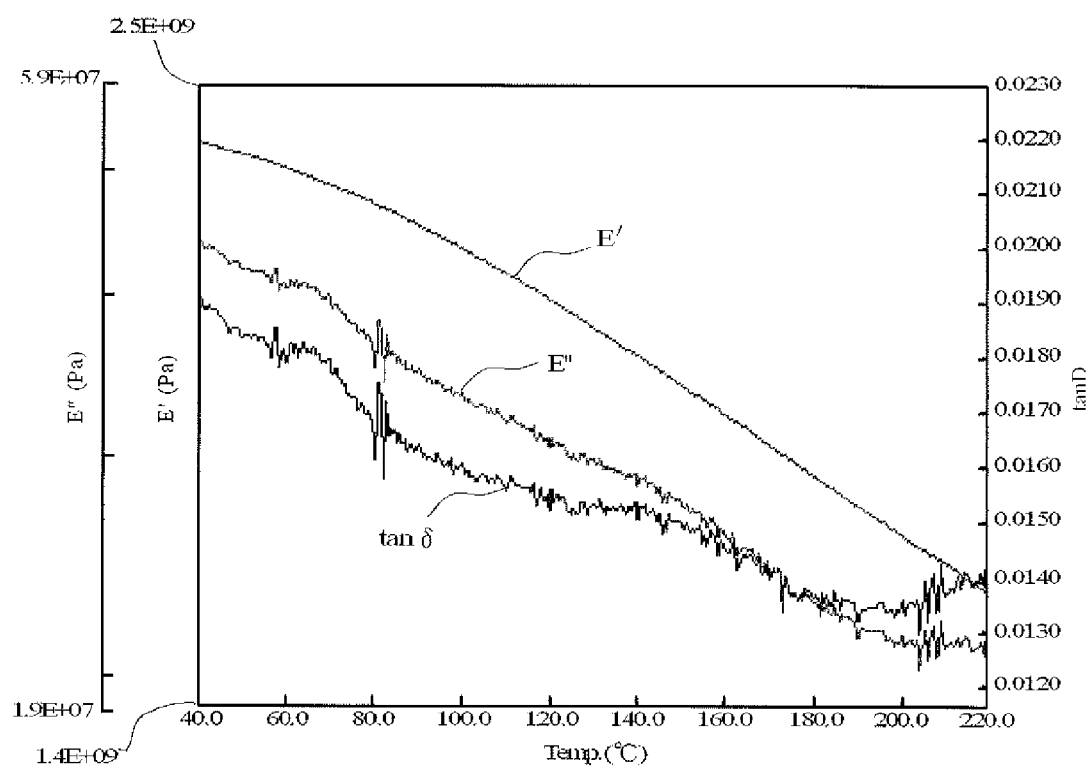
FIG. 5 is a dynamic viscoelasticity chart of a heat-resistant masking tape used for producing the sheet-shaped test piece.

A commercially available adhesive sheet (heat-resistant masking tape 5413, Sumitomo 3M Limited) in which a peroxide-curable type silicone adhesion layer was formed on a polyimide film, which was used in the following Examples and Comparative Examples, itself was subjected to the dynamic viscoelasticity measurement under the following conditions. The obtained results are shown in FIG. 5.
 Measuring Device: DMS 6100, Seiko Instruments Inc.
 Measurement Temperature: 40 to 220° C.
 Heating Rate: 5° C./minute
 Measurement Frequency: 10 Hz
 Deformation Mode: Sine wave tensile mode As shown in FIG. 5, no maximum peak of loss tangent tan δ was observed in the measurement temperature range, which indicated that this masking tape was suitable for the dynamic viscoelasticity measurement of a particulate material that was assumed to have the maximum peak of loss tangent tan δ in the measurement temperature range of from 40 to 220° C.

Reference Example 2

As a particulate material A targeted for the dynamic viscoelasticity measurement, polyurea-urethane-polydivinylbenzene porous particles were manufactured according to Example 1 in Japanese Patent Application Laid-Open No. 2009-221465.

First, 800 parts by mass of distilled water, 0.05 parts by mass of a surfactant (NEWREX R, NOF CORPORATION), and 4 parts by mass of polyvinyl alcohol (PVA-205, Kuraray Co., Ltd.) as a dispersant were put into a 3 L interfacial polymerization container equipped with a thermometer and uniformly mixed to prepare an aqueous phase.

To this aqueous phase, an oil phase in which 70 parts by mass of a trimethylolpropane (1 mole) adduct of methylenediphenyl-4,4'-diisocyanate (3 moles) (D-109, Mitsui Chemicals, Inc.) as a polyfunctional isocyanate compound, 30 parts by mass of divinylbenzene (Merck & Co., Inc.) as a radical polymerizable compound, and a radical polymerization initiator (PEROYL L, NOF CORPORATION) of the equivalent amount (0.3 parts by mass) to 1% by mass of the radical polymerizable compound were dissolved in 100 parts by mass of ethyl acetate was further introduced. The mixture was emulsified by mixing with a homogenizer (10000 rpm/5 minutes: T-50, IKA Japan K.K.), followed by interfacial polymerization and radical polymerization at 80° C. for 6 hours. After the reaction completed, the polymerization reaction solution was allowed to cool to the room temperature, and polymer particles were filtered off and air-dried to give 40 parts by mass of spherical porous resin particles (particulate material A) having a particle size of about 4 μm.

Reference Example 3

As a particulate material B targeted for the dynamic viscoelasticity measurement, polyurea-urethane-polydivinylbenzene porous type aluminum chelate curing catalyst particles were manufactured according to Example 1 in Japanese Patent Application Laid-Open No. 2009-221465. In the curing catalyst particles, an aluminum chelating agent was carried in pores of the porous resin particles (particulate material A) of Reference Example 2.

First, an aqueous phase was prepared in the same manner as in Reference Example 2.

To this aqueous phase, an oil phase in which 100 parts by mass of 24% solution of aluminum monoacetylacetonate bis(ethyl acetoacetate) in isopropanol (Alumichelate D, Kawaken Fine Chemicals Co., Ltd.), 70 parts by mass of a trimethylolpropane (1 mole) adduct of methylenediphenyl-4,4'-diisocyanate (3 moles) (D-109, Mitsui Chemicals, Inc.) as a polyfunctional isocyanate compound, 30 parts by mass of divinylbenzene (Merck & Co., Inc.) as a radical polymerizable compound, and 0.3 parts by mass (equivalent amount to 1% by mass of the radical polymerizable compound) of a radical polymerization initiator (PEROYL L, NOF CORPORATION) were dissolved in 100 parts by mass of ethyl acetate was further introduced. The mixture was emulsified by mixing with a homogenizer (10000 rpm/5 minutes: T-50, IKA Japan K.K.), followed by interfacial polymerization and radical polymerization at 80° C. for 6 hours. After the reaction completed, the polymerization reaction solution was allowed to cool to the room temperature, and polymer particles were filtered off and air-dried to give 80 parts by mass of spherical aluminum chelate curing catalyst particles (particulate material B) having a particle size of about 3 μm.

Reference Example 4

As a particulate material C targeted for the dynamic viscoelasticity measurement, polyurea-urethane porous type aluminum chelate curing catalyst particles were manufactured according to Example 1 in Japanese Patent No. 4381255.

First, 800 parts by mass of distilled water, 0.05 parts by mass of a surfactant (NEWREX R, NOF CORPORATION), and 4 parts by mass of polyvinyl alcohol (PVA-205, Kuraray Co., Ltd.) as a dispersant were put into a 3 L interfacial polymerization container equipped with a thermometer and uniformly mixed to prepare an aqueous phase. To this aqueous phase, an oil phase in which 11 parts by mass of 24% solution of aluminum monoacetylacetonate bis(ethyl acetoacetate) in isopropanol (Alumichelate D, Kawaken Fine Chemicals Co., Ltd.) and 11 parts by mass of a trimethylolpropane (1 mole) adduct of methylene diphenyl-4,4'-diisocyanate (3 moles) (D-109, Mitsui Chemicals, Inc.) were dissolved in 30 parts by mass of ethyl acetate were further introduced. The mixture was emulsified by mixing with a homogenizer (11000 rpm/10 minutes: T-25, IKA Japan K.K.), followed by interfacial polymerization at 60° C. overnight. After the reaction completed, the polymerization reaction solution was allowed to cool to the room temperature, and interfacially-polymerized particles were filtered off and air-dried to give 20 parts by mass of spherical aluminum chelate curing catalyst particles (particulate material C) having a particle size of about 10 μm.

Example 1

Figure 6A:
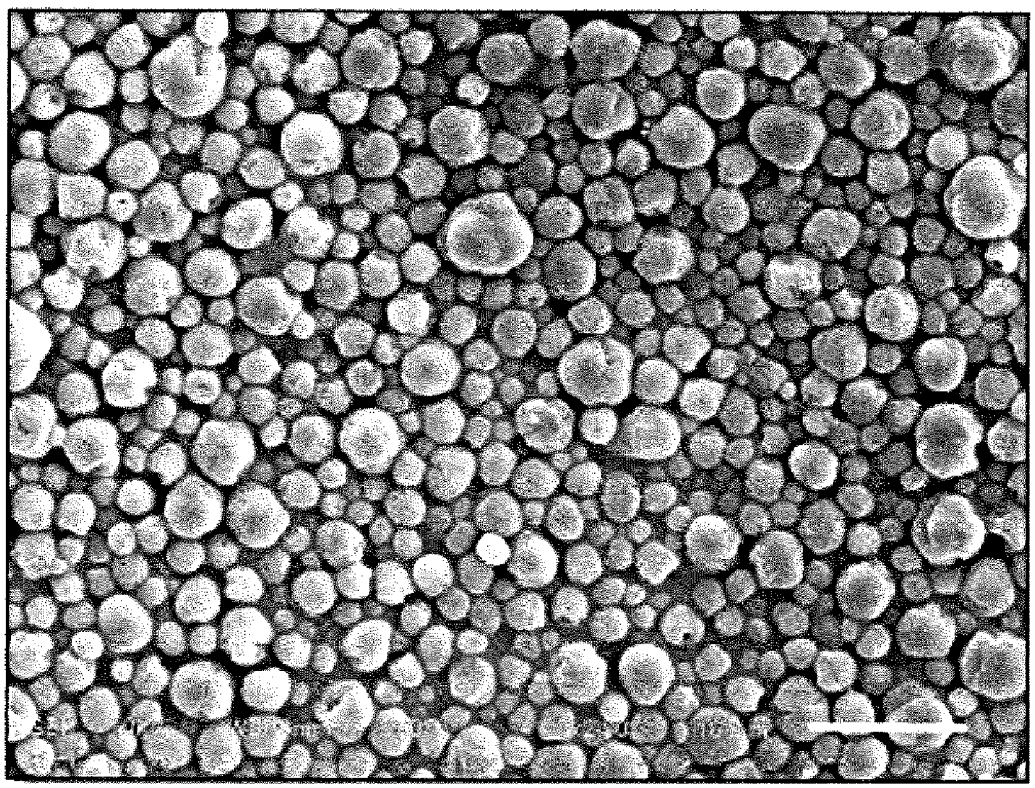
FIG. 6A is a scanning electron micrograph (magnification of 2000 times) of the particulate material attached surface of a sheet-shaped test piece used in Example 1.
Figure 6B:
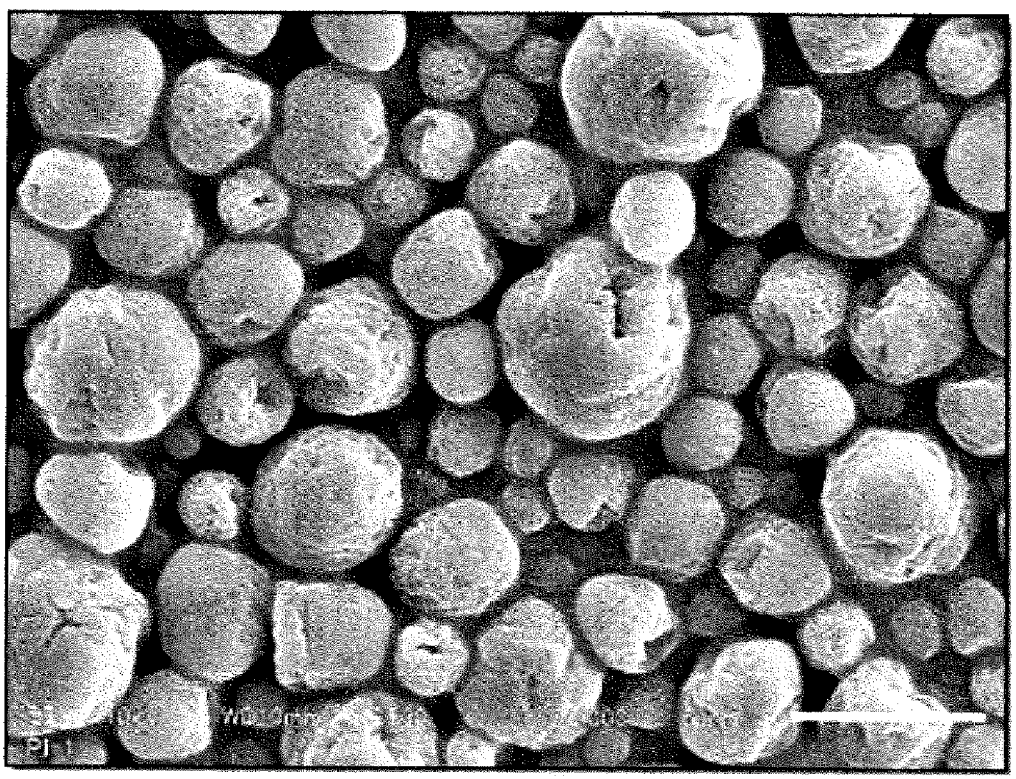
FIG. 6B is a scanning electron micrograph (magnification of 5000 times) of the particulate material attached surface of the sheet-shaped test piece used in Example 1.

On a flat table, a heat-resistant masking tape (5413, Sumitomo 3M Limited) which has a peroxide-curable type silicone adhesion layer formed on a polyimide film base material and a total thickness of 66 μm was placed with the adhesion layer facing upward. Then the particulate material A was sprinkled on the exposed adhesion layer using a spatula. After sprinkling, the surface was squeegeed using a clean wiper (FF-390C, Kuraray Kuraflex Co., Ltd.) and then air-blown. This gave a sheet-shaped test piece for the dynamic viscoelasticity measurement of the particulate material A. The scanning electron micrographs of this sheet-shaped test piece are shown in FIG. 6A (magnification of 2000 times) and FIG. 6B (magnification of 5000 times). These micrographs show that most of the particulate material A was attached to the adhesion layer in a single layer.

Figure 7A:
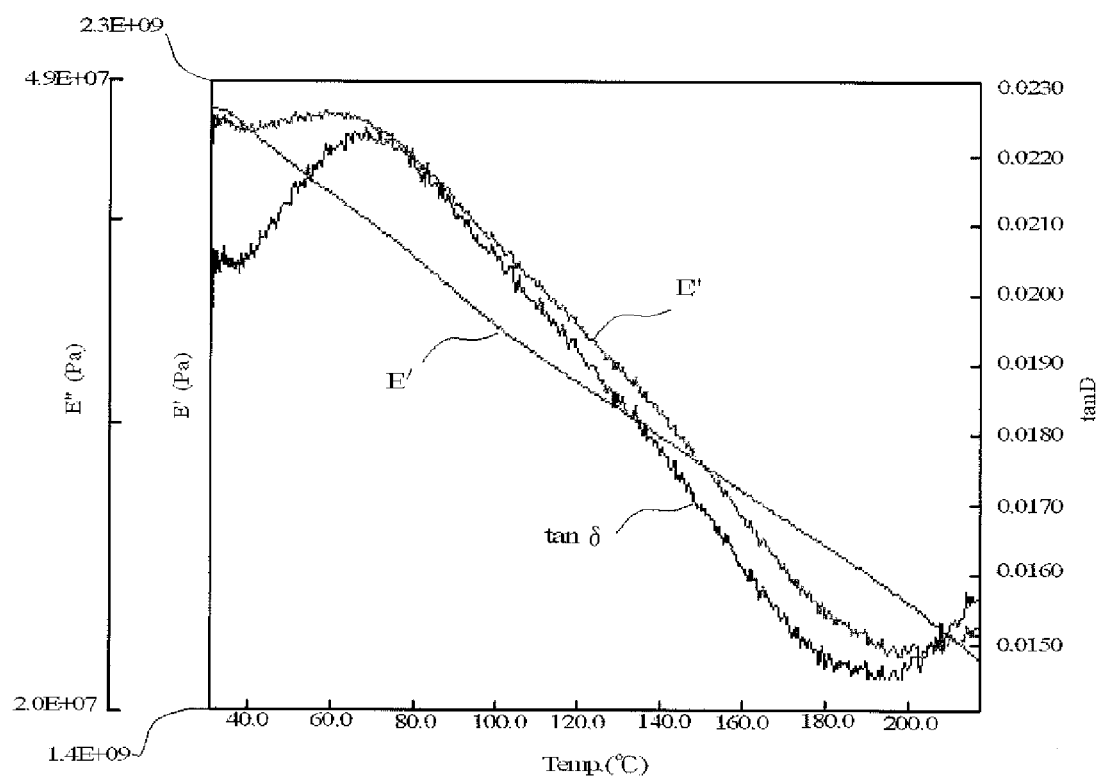
FIG. 7A is a dynamic viscoelasticity chart of the sheet-shaped test piece used in Example 1.

The obtained sheet-shaped test piece was subjected to the dynamic viscoelasticity test in the same manner as in Reference Example 1 and the obtained dynamic viscoelasticity chart is shown in FIG. 7A. As shown in FIG. 7A, the maximum peak of loss tangent tan δ originated from the particulate material A was observed and the temperature at the maximum peak was 69.2° C. (glass transition temperature).

Figure 7B:
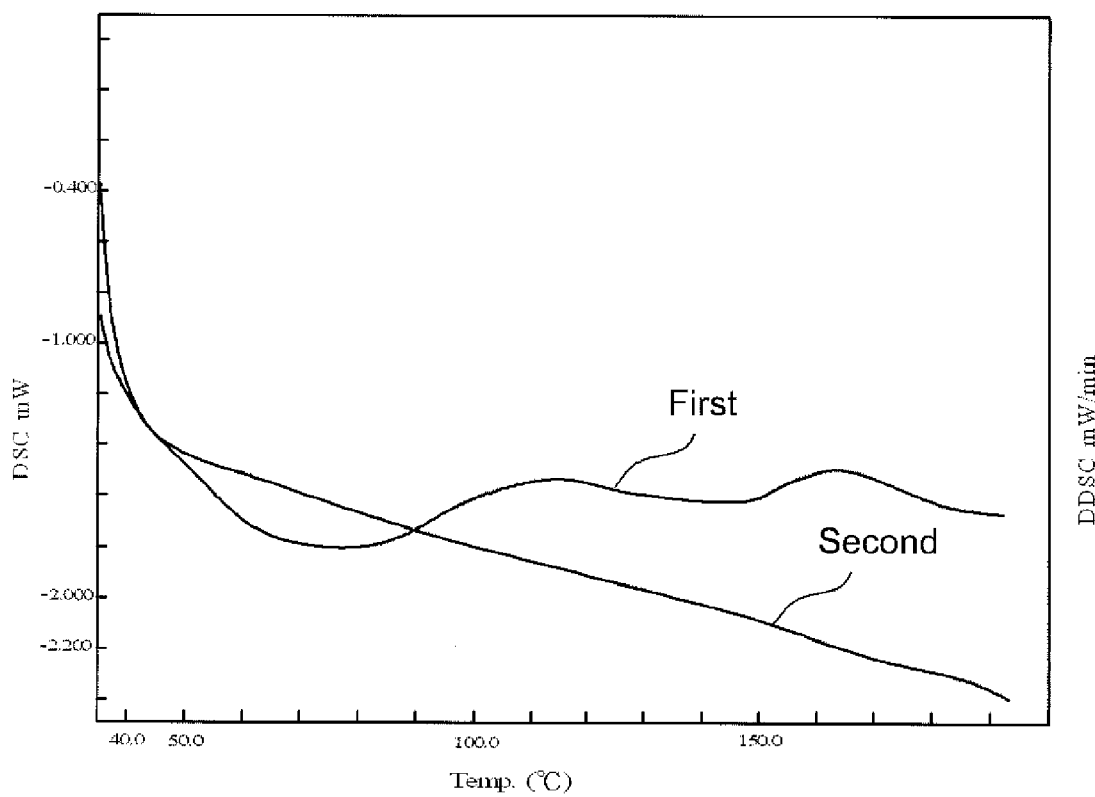
FIG. 7B is a DSC chart of the sheet-shaped test piece used in Example 1.

In order to remove the influence of a residual monomer or a residual solvent, the obtained sheet-shaped test piece was once thermally analyzed using a differential scanning calorimetry (DSC) device (DSC 6200, Seiko Instruments Inc.) (measured amount of 5 mg; heating rate of 10° C./minute), then allowed to cool, and thermally analyzed for the second time. The obtained DSC chart is shown in FIG. 7B. FIG. 7B shows that no inflection point was observed in the second DSC chart. It was thus found that it was impossible to measure the glass transition temperature of the particulate material A with DSC.

Example 2

Figure 8A:
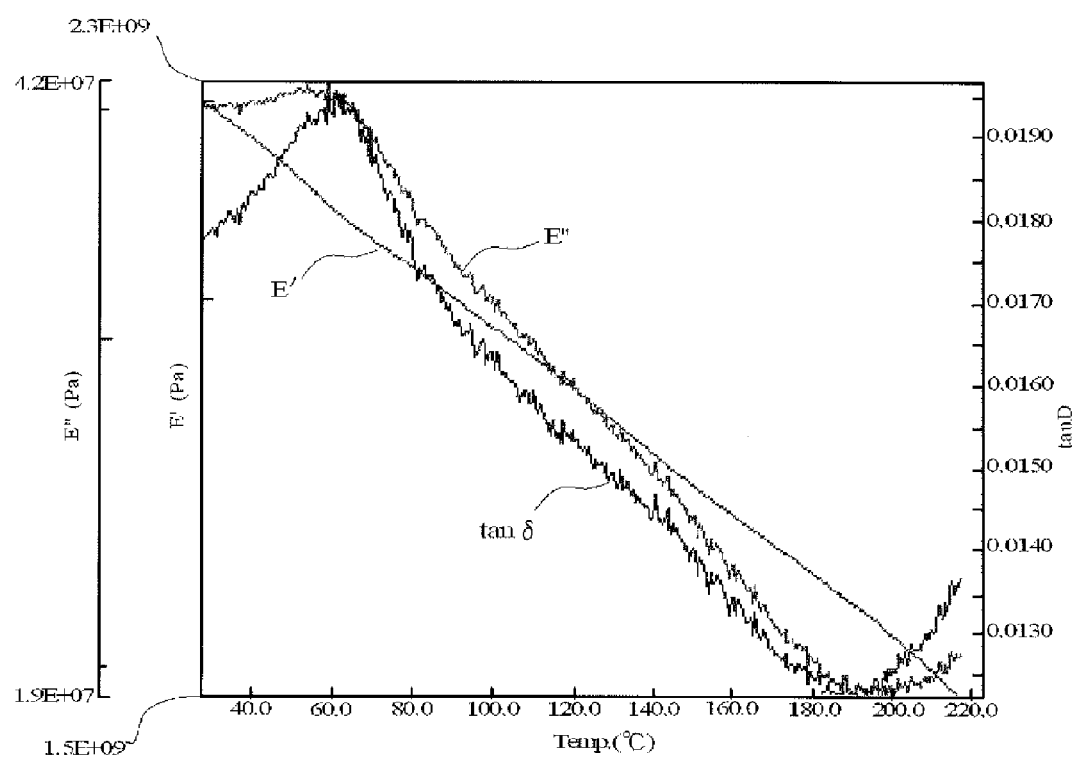
FIG. 8A is a dynamic viscoelasticity chart of a sheet-shaped test piece used in Example 2.

A sheet-shaped test piece was produced in the same manner as in Example 1 except that the particulate material B of Reference Example 3 was used instead of the particulate material A, and subjected to the dynamic viscoelasticity measurement. The obtained results are shown in FIG. 8A. As shown in FIG. 8A, the maximum peak of loss tangent tan δ originated from the particulate material B was observed and the temperature at the maximum peak was 63.5° C. (glass transition temperature). In consideration of this result and the result of Example 1, it was found that polymerized walls were plasticized and the glass transition temperature decreased by about 5° C. when an aluminum chelating agent was carried by porous resin particles.

Figure 8B:
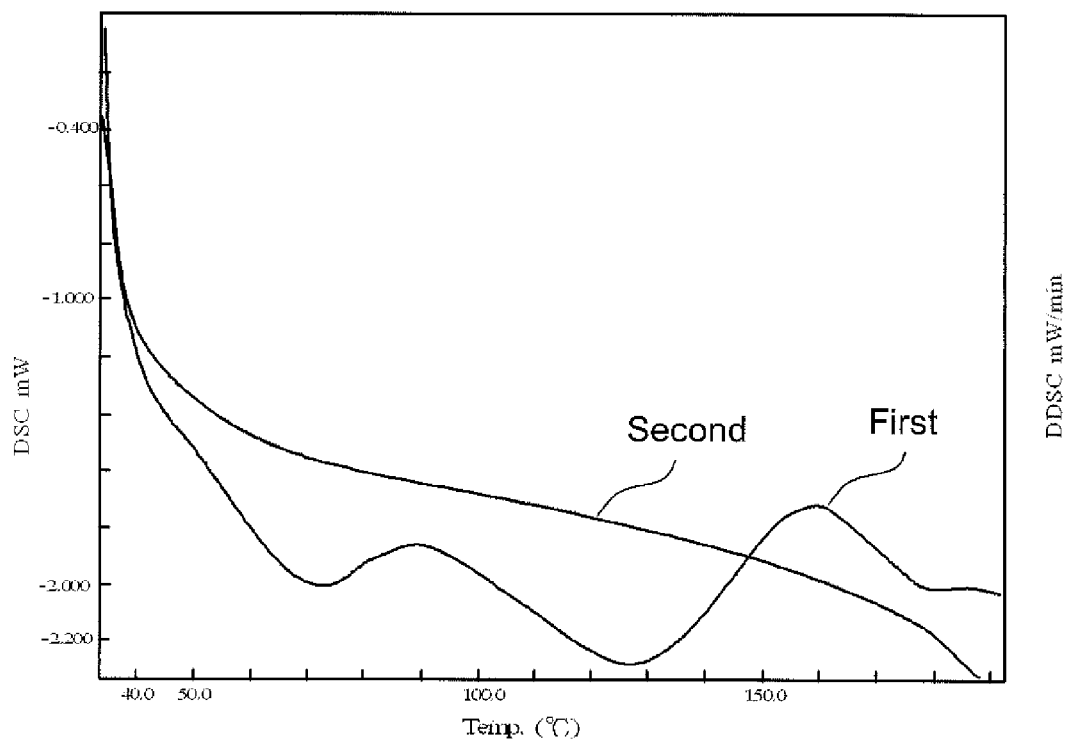
FIG. 8B is a DSC chart of the sheet-shaped test piece used in Example 2.

In order to remove the influence of a residual monomer or a residual solvent, the obtained sheet-shaped test piece was once thermally analyzed using a differential scanning calorimetry (DSC) device (DSC 6200, Seiko Instruments Inc.) (measured amount of 5 mg; heating rate of 10° C./minute), then allowed to cool, and thermally analyzed for the second time. The obtained DSC chart is shown in FIG. 8B. FIG. 8B shows that no inflection point was observed in the second DSC chart. It was thus found that it was impossible to measure the glass transition temperature of the particulate material B with DSC.

Examples 3 and 4

A half of the particulate material C of Reference Example 4 was crushed using a jet mill (AO-JET MILL, Seishin Enterprise Co., Ltd.) to produce primary particles as a particulate material D. The particle size distribution of each of the particulate materials C and D was measured using a particle size distribution analyzer (SD-2000, Sysmex Corporation). The obtained results (on a volume basis) are shown in FIG. 9A (particulate material C) and FIG. 10A (particulate material D). From FIGS. 9A and 10A, the CV value (%) of particle size distribution of the non-crushed particulate material C was 72.1% and the CV value (%) of particle size distribution of the crushed particulate material D was 31.8%.

Figure 9B:
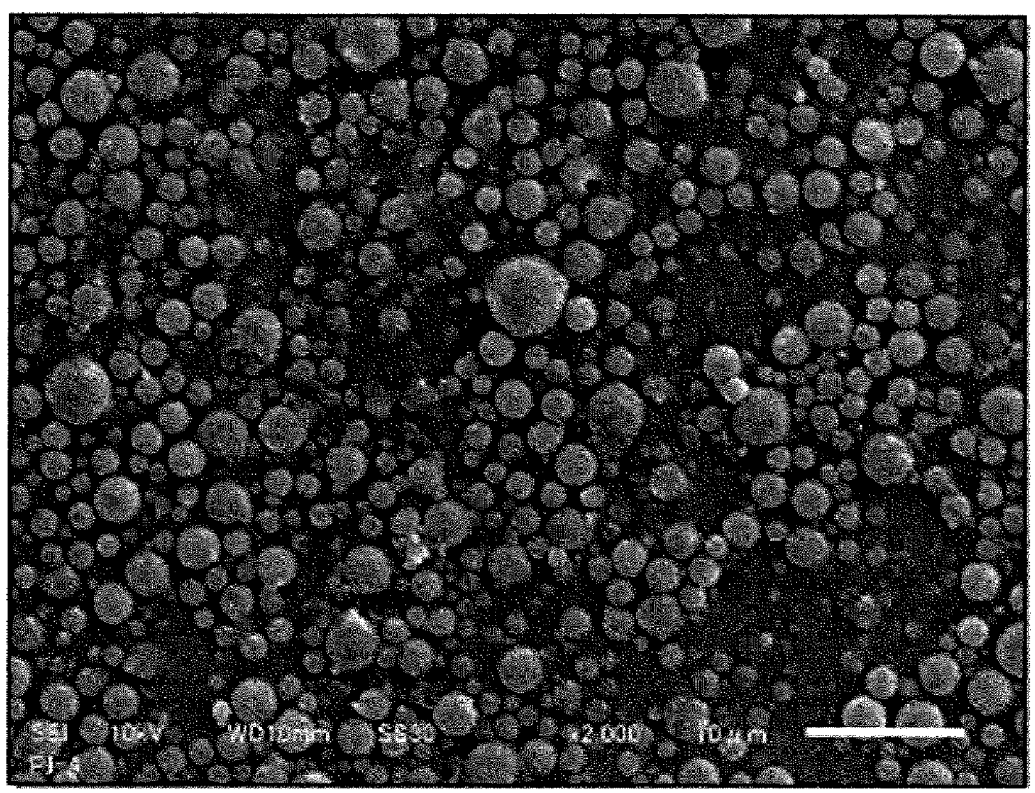
FIG. 9B is a scanning electron micrograph (magnification of 2000 times) of the particulate material attached surface of a sheet-shaped test piece used in Example 3.
Figure 10A:
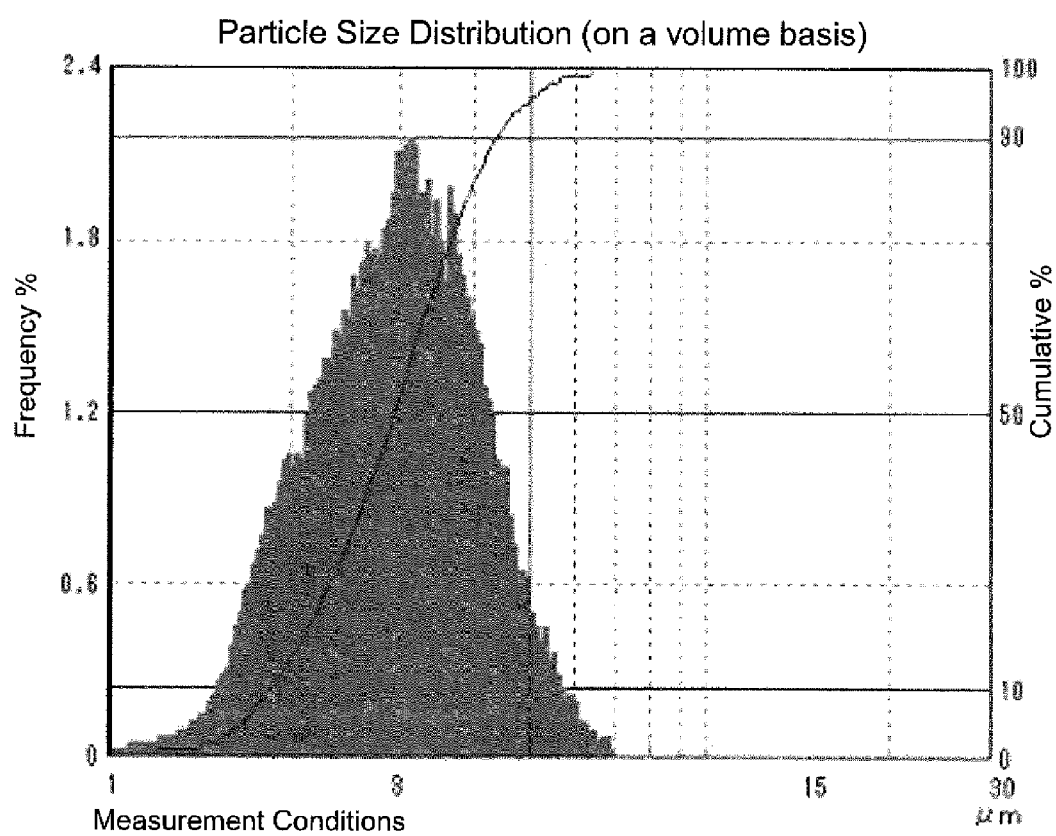
FIG. 10A is a particle size distribution chart on a volume basis of a particulate material D used in Example 4.
Figure 10B:
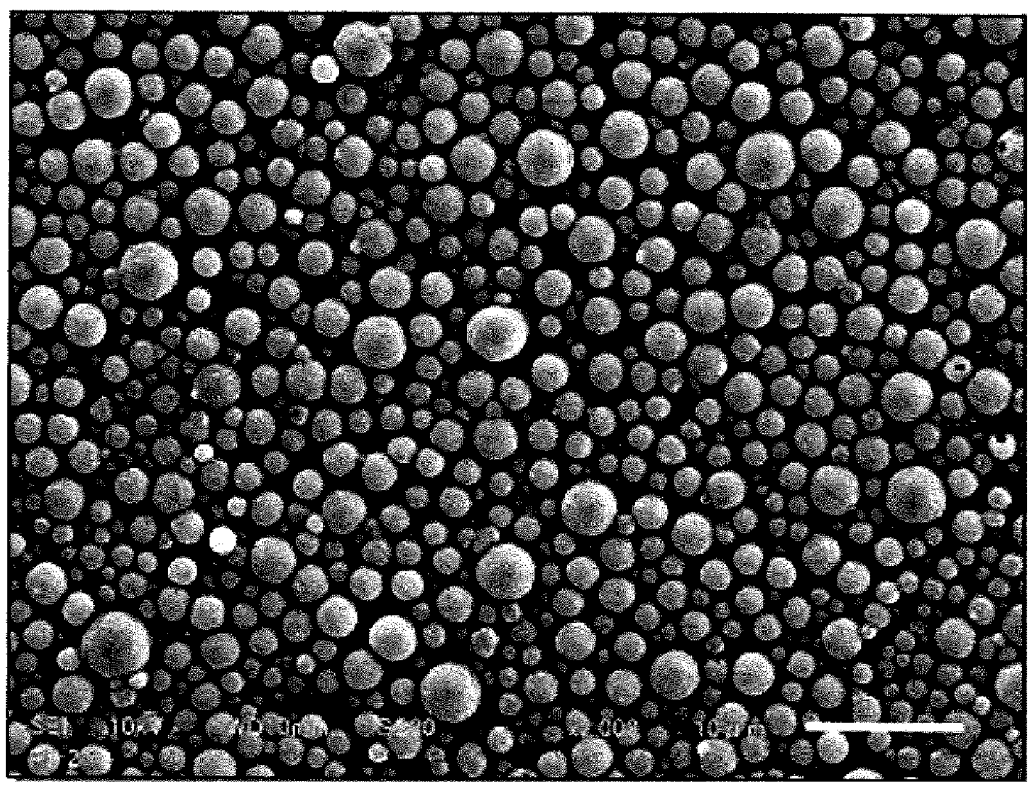
FIG. 10B is a scanning electron micrograph (magnification of 2000 times) of the particulate material attached surface of a sheet-shaped test piece used in Example 4.
Figure 11:
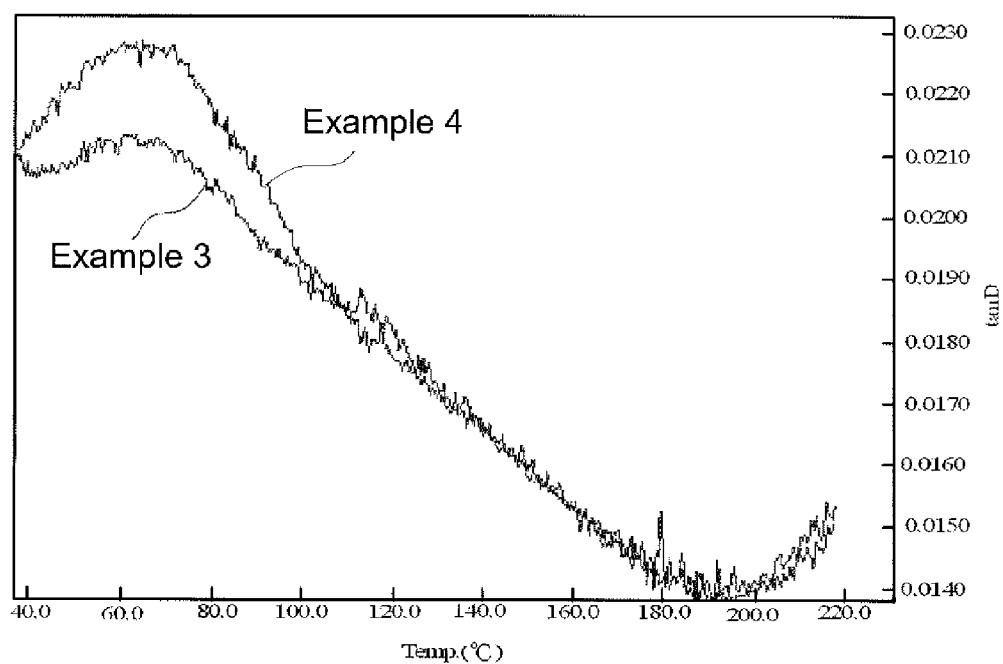
FIG. 11 is a dynamic viscoelasticity chart of the sheet-shaped test pieces used in Examples 3 and 4.

Sheet-shaped test pieces were produced in the same manner as in Example 1 except that the particulate material C (Example 3) or the particulate material D (Example 4) was used instead of the particulate material A, and subjected to the dynamic viscoelasticity measurement. The scanning electron micrographs of these sheet-shaped test pieces are shown in FIG. 9B (Example 3, magnification of 2000 times) and FIG. 10B (Example 4, magnification of 2000 times). The obtained results of the dynamic viscoelasticity measurement are shown in FIG. 11. As shown in FIG. 11, the maximum peaks of loss tangent tan δ originated from the particulate materials C and D were observed and the temperatures of the maximum peaks were 64.6° C. for the particulate material C and 65.1° C. for the particulate material D, respectively. Although there was no significant difference between both, the particulate material C in which relatively many large aggregates were present tends to have a broad maximum peak of loss tangent tan δ.

Reference Example 5

Figure 12A:
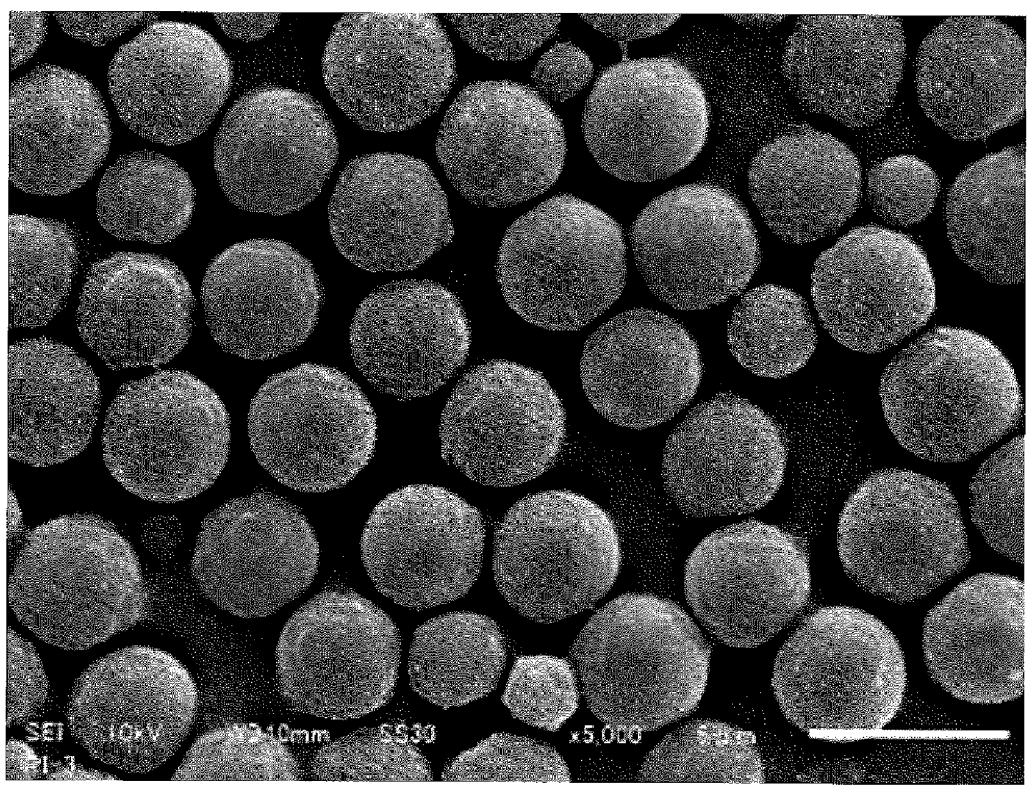
FIG. 12A is a scanning electron micrograph (magnification of 5000 times) of the particulate material attached surface of a sheet-shaped test piece used in Reference Example 5.
Figure 12B:
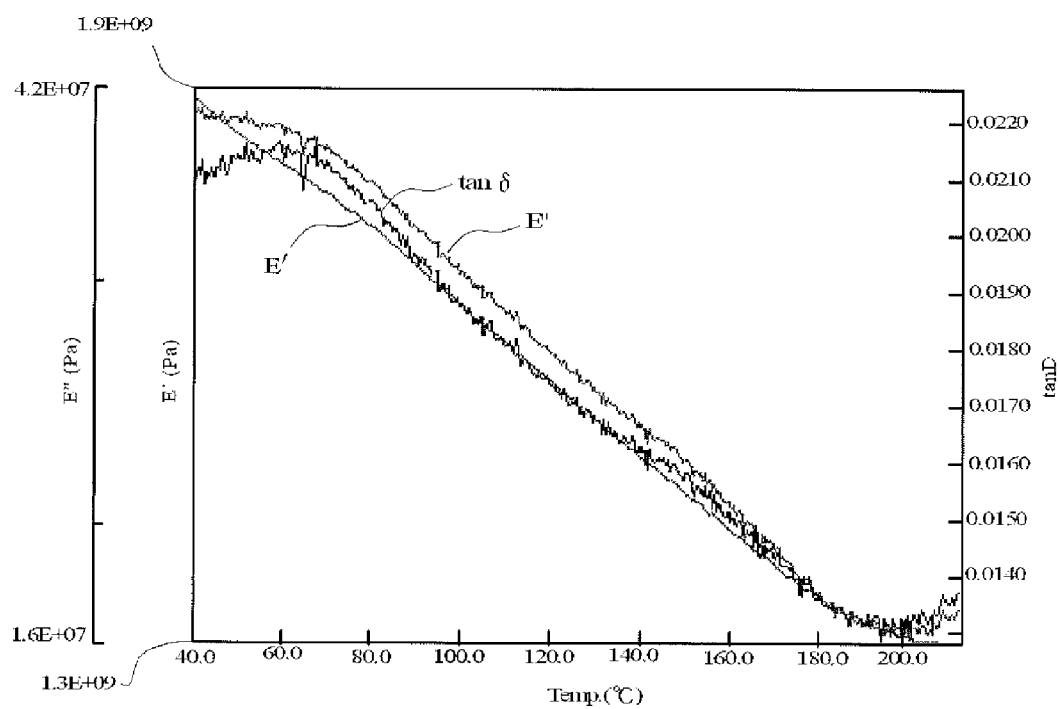
FIG. 12B is a dynamic viscoelasticity chart of the sheet-shaped test piece of Reference Example 5 using monodisperse acrylic polymer particles having a CV value of 6.89%.

A sheet-shaped test piece was produced in the same manner as in Example 1 except that monodisperse acrylic polymer particles having a CV value (%) of particle size distribution of 6.89% (Art Pearl J-5P, Negami Chemical Industrial Co., Ltd.) was used instead of the particulate material A, and subjected to the dynamic viscoelasticity measurement. The scanning electron micrograph of this sheet-shaped test piece is shown in FIG. 12A (magnification of 5000 times). The obtained results of the dynamic viscoelasticity measurement are shown in FIG. 12E. As shown in FIG. 12B, it was found that the maximum peak of loss tangent tan δ is much broader than those in Examples 3 and 4 having a CV value of 30% or more.

INDUSTRIAL APPLICABILITY

The method for measuring a dynamic viscoelasticity of the present invention uses the sheet-shaped test piece in which a particulate material to be measured is attached to an adhesion layer of a heat-resistant sheet base material having the adhesion layer formed thereon as a sample to be subjected to the dynamic viscoelasticity measurement. This sheet-shaped test piece can be simply produced by a procedure such as sprinkling using a very small amount of the particulate material in a short time with low cost, and further a cheap, commercially available masking tape can be used as a sheet material having an adhesion layer formed on a heat-resistant sheet base material. Therefore, the present invention is useful for a dynamic viscoelasticity measurement of a particulate material because it is possible to shorten the time for the dynamic viscoelasticity measurement including the production time of the sheet-shaped test piece and also reduce the cost for the measurement.

REFERENCE SIGNS LIST

1 Heat-resistant sheet base material
2 Adhesion layer
3, 3' Particulate material
4 Sieve
5 Squeegee
6 Air nozzle
10 Sheet-shaped test piece

The invention claimed is:

1. A method for measuring a dynamic viscoelasticity of a particulate material, the method comprising:
   subjecting a sheet-shaped test piece as a sample to dynamic viscoelasticity measurement,
   the sheet-shaped test piece comprising a heat-resistant sheet base material, an adhesion layer, and a particulate material to be measured, and
   the adhesion layer being formed on the heat-resistant sheet base material, and the particulate material being attached to the adhesion layer;
   performing the dynamic viscoelasticity measurement, which is a temperature dependent measurement, under the following measurement conditions:
      a measurement temperature is within a predetermined temperature range of from −150 to 300° C.;
      a heating rate is a constant rate ranging from 0.01 to 100° C./minute;
      a measurement frequency is a constant frequency ranging from 0.01 to 100 Hz; and
      using a sine wave control tensile mode; and
   forming each of the adhesion layer and the heat-resistant sheet base material each from a material having a maximum peak top of loss tangent tan δ that does not overlap with a maximum peak top of loss tangent tan δ of the particulate material to be measured in the measurement temperature range of the dynamic viscoelasticity measurement.

2. The method for measuring a dynamic viscoelasticity according to claim 1, further comprising:
   attaching the particulate material crushed in advance to the adhesion layer.

3. The method for measuring a dynamic viscoelasticity according to claim 1, further comprising:
   sprinkling the particulate material on one side of the adhesion layer; and
   then squeegeeing and/or the air-blowing particulate material-sprinkled surface when the particulate material is attached to the adhesion layer.

4. The method for measuring a dynamic viscoelasticity according to claim 1, further comprising:
   measuring loss tangent tan δ as the dynamic viscoelasticity measurement.

5. The method for measuring a dynamic viscoelasticity according to claim 1 wherein the adhesion layer to be used is formed from a silicone adhesive using peroxide as a curing agent and the heat-resistant sheet base material to be used is formed from a polyimide resin when the measurement temperature range of the dynamic viscoelasticity measurement is from −50 to 250° C.

6. The method for measuring a dynamic viscoelasticity according to claim 1, wherein resin particles having a coefficient of variance (CV value) of particle size distribution of 5% to 70% are used as the particulate material.

7. The method for measuring a dynamic viscoelasticity according to claim 6, wherein the particulate material is a particulate material in which an aluminum chelating agent is carried by porous resin particles obtained by interfacially polymerizing a polyfunctional isocyanate.

8. A method for measuring a dynamic viscoelasticity of a particulate material, the method comprising:
   subjecting a sheet-shaped test piece as a sample to dynamic viscoelasticity measurement,
   the sheet-shaped test piece comprising a heat-resistant sheet base material, an adhesion layer, and a particulate material to be measured, and
   the adhesion layer being formed on the heat-resistant sheet base material, and the particulate material being attached to the adhesion layer;
   wherein resin particles having a coefficient of variance (CV value) of particle size distribution of 5% to 70% are used as the particulate material, and
   wherein the particulate material is a particulate material in which an aluminum chelating agent is carried by porous resin particles obtained by interfacially polymerizing a polyfunctional isocyanate.

* * * * *